US012567495B2

(12) United States Patent
Malekmohammadi et al.

(10) Patent No.: US 12,567,495 B2
(45) Date of Patent: Mar. 3, 2026

(54) NEUROANATOMY-BASED SEARCH TO OPTIMIZE TRAJECTORY SELECTION DURING DBS TARGETING

(71) Applicant: Boston Scientific Neuromodulation Corporation, Valencia, CA (US)

(72) Inventors: Mahsa Malekmohammadi, Sherman Oaks, CA (US); Lisa Moore, Glendale, CA (US); G. Karl Steinke, Valencia, CA (US); Raul Serrano Carmona, Venice, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 287 days.

(21) Appl. No.: 18/488,684

(22) Filed: Oct. 17, 2023

(65) Prior Publication Data

US 2024/0136047 A1    Apr. 25, 2024
US 2024/0233907 A9    Jul. 11, 2024

Related U.S. Application Data

(60) Provisional application No. 63/380,099, filed on Oct. 19, 2022.

(51) Int. Cl.
*G16H 20/40*        (2018.01)
*A61N 1/36*         (2006.01)

(52) U.S. Cl.
CPC ......... *G16H 20/40* (2018.01); *A61N 1/36125* (2013.01); *A61N 1/36146* (2013.01)

(58) Field of Classification Search
None
See application file for complete search history.

(56) References Cited

U.S. PATENT DOCUMENTS

| | | | |
|---|---|---|---|
| 6,052,624 | A | 4/2000 | Mann |
| 6,181,969 | B1 | 1/2001 | Gord |
| 6,393,325 | B1 | 5/2002 | Mann et al. |
| 6,490,486 | B1 | 12/2002 | Bradley |
| 6,609,032 | B1 | 8/2003 | Woods et al. |
| 6,845,267 | B2 | 1/2005 | Harrison et al. |

(Continued)

FOREIGN PATENT DOCUMENTS

| | | |
|---|---|---|
| AU | 2014351064 | 6/2016 |
| AU | 2019216650 | 9/2019 |

(Continued)

OTHER PUBLICATIONS

Qian, Xing, et al., "A Method for Removal of Deep Brain Stimulation Artifact From Local Field Potentials," IEEE Transactions On Neural Systems and Rehabilitation Engineering, vol. 25, No. 12, Dec. 2017, 10 pages.

(Continued)

*Primary Examiner* — Michael W Kahelin

(74) *Attorney, Agent, or Firm* — Lewis & Reese, PLLC

(57)            ABSTRACT

Methods and systems for planning a trajectory for implanting electrical stimulation leads in a patient's brain are described. The methods and systems rank candidate trajectories based on their expected therapeutic efficacies, as well as other criteria. Optimized stimulation parameters are determined for each of the candidate trajectories and therapeutic efficacies using the optimized parameters are predicted.

18 Claims, 8 Drawing Sheets

(56) References Cited

U.S. PATENT DOCUMENTS

| | | |
|---|---|---|
| 6,909,917 B2 | 6/2005 | Woods et al. |
| 6,950,707 B2 | 9/2005 | Whitehurst |
| 7,555,346 B1 | 6/2009 | Woods et al. |
| 7,582,062 B2 | 9/2009 | Magill et al. |
| 7,831,307 B1 | 11/2010 | Moffitt |
| 7,930,030 B2 | 4/2011 | Woods et al. |
| 8,121,701 B2 | 2/2012 | Woods et al. |
| 8,180,601 B2 | 5/2012 | Butson et al. |
| 8,265,762 B2 | 9/2012 | Woods et al. |
| 8,401,658 B2 | 3/2013 | Woods et al. |
| 8,606,362 B2 | 12/2013 | He et al. |
| 8,620,436 B2 | 12/2013 | Parramon et al. |
| 8,805,524 B2 | 8/2014 | Woods et al. |
| 8,812,124 B2 | 8/2014 | Lee |
| 8,855,773 B2 | 10/2014 | Kokones et al. |
| 8,868,193 B2 | 10/2014 | Ranu et al. |
| 8,868,196 B2 | 10/2014 | Lee et al. |
| 8,868,197 B2 | 10/2014 | Lee |
| 8,909,350 B2 | 12/2014 | Lee |
| 8,914,119 B2 | 12/2014 | Wu et al. |
| 8,958,615 B2 | 2/2015 | Blum et al. |
| 9,014,820 B2 | 4/2015 | Lee et al. |
| 9,050,473 B2 | 6/2015 | Woods et al. |
| 9,072,905 B2 | 7/2015 | Kokones et al. |
| 9,205,261 B2 | 12/2015 | Kim et al. |
| 9,248,280 B2 | 2/2016 | Moffitt et al. |
| 9,381,356 B2 | 7/2016 | Parker et al. |
| 9,387,328 B2 | 7/2016 | Lee |
| 9,387,334 B2 | 7/2016 | Lee et al. |
| 9,411,935 B2 | 8/2016 | Moffitt et al. |
| 9,511,231 B1 | 12/2016 | Kent et al. |
| 10,183,167 B2 | 1/2019 | Steinke et al. |
| 10,183,168 B2 | 1/2019 | Baru et al. |
| 10,195,439 B2 | 2/2019 | Steinke et al. |
| 10,207,113 B2 | 2/2019 | Lee et al. |
| 10,207,114 B2 | 2/2019 | Lee |
| 10,249,041 B2 | 4/2019 | Varkuti |
| 10,252,059 B2 | 4/2019 | Steinke et al. |
| 10,286,205 B2 | 5/2019 | Steinke et al. |
| 10,406,368 B2 | 9/2019 | Hershey et al. |
| 10,463,860 B2 | 11/2019 | Sinclair et al. |
| 10,549,097 B2 | 2/2020 | Zhang et al. |
| 10,576,292 B2 | 3/2020 | Orinski |
| 10,974,051 B2 | 4/2021 | Steinke et al. |
| 10,994,131 B2 | 5/2021 | Durand et al. |
| 11,020,004 B2 * | 6/2021 | Varkuti ................. G16H 20/30 |
| 11,123,563 B2 | 9/2021 | Mustakos et al. |
| 11,195,609 B2 | 12/2021 | Mustakos et al. |
| 11,344,732 B2 | 5/2022 | Moffitt et al. |
| 11,376,433 B2 | 7/2022 | Zhang et al. |
| 11,478,633 B2 | 10/2022 | Tinkhauser et al. |
| 2005/0065427 A1 | 3/2005 | Magill et al. |
| 2006/0224222 A1 | 10/2006 | Bradley et al. |
| 2007/0244407 A1 | 10/2007 | Osorio |
| 2009/0118786 A1 | 5/2009 | Meadows et al. |
| 2009/0118787 A1 | 5/2009 | Moffitt et al. |
| 2009/0299421 A1 | 12/2009 | Sawchuk |
| 2010/0305660 A1 | 12/2010 | Hegi et al. |
| 2011/0105939 A1 | 5/2011 | Yong et al. |
| 2012/0046712 A1 | 2/2012 | Woods et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2013/0289660 A1 * | 10/2013 | Molnar ................ A61B 5/4893 607/59 |
| 2013/0289665 A1 | 10/2013 | Marnfeldt et al. |
| 2014/0163639 A1 | 6/2014 | Zhu |
| 2014/0243926 A1 | 8/2014 | Carcieri |
| 2014/0277282 A1 | 9/2014 | Jaax |
| 2014/0296737 A1 | 10/2014 | Parker et al. |
| 2014/0350634 A1 | 11/2014 | Grill et al. |
| 2014/0378941 A1 | 12/2014 | Su et al. |
| 2015/0039048 A1 | 2/2015 | Woods et al. |
| 2015/0066108 A1 | 3/2015 | Shi et al. |
| 2015/0080982 A1 | 3/2015 | Funderburk |

| | | |
|---|---|---|
| 2015/0088228 A1 | 3/2015 | Moffitt |
| 2015/0157861 A1 | 6/2015 | Aghassian |
| 2015/0231402 A1 | 8/2015 | Aghassian |
| 2015/0360033 A1 | 12/2015 | Koubeissi et al. |
| 2015/0360038 A1 | 12/2015 | Zottola et al. |
| 2016/0045747 A1 | 2/2016 | Jiang et al. |
| 2016/0158565 A1 | 6/2016 | Lee |
| 2016/0287126 A1 | 10/2016 | Parker et al. |
| 2016/0339251 A1 | 11/2016 | Kent et al. |
| 2016/0361542 A1 | 12/2016 | Kaula et al. |
| 2017/0120056 A1 | 5/2017 | Woods et al. |
| 2017/0128019 A1 | 5/2017 | Shao et al. |
| 2017/0189687 A1 | 7/2017 | Steinke et al. |
| 2017/0189689 A1 | 7/2017 | Steinke et al. |
| 2017/0281959 A1 | 10/2017 | Serrano Carmona et al. |
| 2017/0333701 A1 | 11/2017 | Bradley et al. |
| 2017/0333715 A1 | 11/2017 | De Ridder et al. |
| 2018/0071513 A1 | 3/2018 | Weiss et al. |
| 2018/0071520 A1 | 3/2018 | Weerakoon et al. |
| 2018/0071527 A1 | 3/2018 | Feldman et al. |
| 2018/0110987 A1 | 4/2018 | Parker |
| 2018/0132747 A1 | 5/2018 | Parker et al. |
| 2018/0133459 A1 | 5/2018 | Parker et al. |
| 2018/0140831 A1 | 5/2018 | Feldman et al. |
| 2018/0140843 A1 | 5/2018 | Kent et al. |
| 2018/0221644 A1 | 8/2018 | Grill et al. |
| 2019/0030323 A1 | 1/2019 | Koka et al. |
| 2019/0038902 A1 | 2/2019 | Kaemmerer et al. |
| 2019/0070418 A1 | 3/2019 | Hincapie Ordonez et al. |
| 2019/0076645 A1 | 3/2019 | Bower et al. |
| 2019/0083796 A1 | 3/2019 | Weerakoon et al. |
| 2019/0099602 A1 | 4/2019 | Esteller et al. |
| 2019/0143120 A1 | 5/2019 | Sinclair et al. |
| 2019/0175915 A1 | 6/2019 | Brill et al. |
| 2019/0209844 A1 | 7/2019 | Esteller et al. |
| 2019/0209851 A1 | 7/2019 | Kothandaraman et al. |
| 2019/0232062 A1 | 8/2019 | Falowski |
| 2019/0262609 A1 | 8/2019 | Brill et al. |
| 2019/0274637 A1 | 9/2019 | Wilson et al. |
| 2019/0275331 A1 | 9/2019 | Zhu |
| 2019/0299006 A1 | 10/2019 | Marnfeldt |
| 2019/0366094 A1 | 12/2019 | Esteller et al. |
| 2019/0381318 A1 | 12/2019 | Sinclair et al. |
| 2020/0001086 A1 | 1/2020 | Fernandez et al. |
| 2020/0001091 A1 | 1/2020 | Marnfeldt |
| 2020/0038660 A1 | 2/2020 | Torgerson |
| 2020/0138324 A1 | 5/2020 | Sinclair et al. |
| 2020/0147393 A1 | 5/2020 | Zhang et al. |
| 2020/0305744 A1 | 10/2020 | Weerakoon et al. |
| 2020/0305745 A1 | 10/2020 | Wagenbach et al. |
| 2020/0335221 A1 | 10/2020 | Fichtinger et al. |
| 2020/0391037 A1 | 12/2020 | Grado et al. |
| 2021/0016091 A1 | 1/2021 | Parker et al. |
| 2021/0046322 A1 | 2/2021 | Zhang et al. |
| 2021/0121696 A1 | 4/2021 | Parker et al. |
| 2021/0236821 A1 | 8/2021 | Sinclair et al. |
| 2021/0267523 A1 | 9/2021 | Donoghue et al. |
| 2021/0339014 A1 | 11/2021 | Dinsmoor et al. |
| 2021/0343397 A1 * | 11/2021 | Orr ........................ G16H 30/20 |
| 2022/0007987 A1 | 1/2022 | Huang et al. |
| 2022/0040486 A1 | 2/2022 | Moffitt |
| 2022/0054090 A1 | 2/2022 | Brockway et al. |
| 2022/0111213 A1 | 4/2022 | Cassar et al. |
| 2022/0151535 A1 | 5/2022 | Parker et al. |
| 2022/0218995 A1 | 7/2022 | Block et al. |
| 2022/0233866 A1 | 7/2022 | Gururaj et al. |
| 2022/0266022 A1 | 8/2022 | Steinke et al. |
| 2022/0296892 A1 | 9/2022 | Esteller et al. |
| 2022/0296893 A1 | 9/2022 | Steinke et al. |
| 2022/0339448 A1 | 10/2022 | Jayakumar et al. |
| 2023/0023842 A1 | 1/2023 | Steinke et al. |
| 2023/0062062 A1 | 3/2023 | Litvak et al. |
| 2023/0069981 A1 | 3/2023 | Isaacson et al. |
| 2023/0099390 A1 | 3/2023 | Esteller et al. |

(56)                References Cited

U.S. PATENT DOCUMENTS

| 2023/0141183 A1 | 5/2023 | Moore et al. |
| 2023/0201597 A1 | 6/2023 | Haddock et al. |
| 2023/0271015 A1 | 8/2023 | Malekmohammadi et al. |

FOREIGN PATENT DOCUMENTS

| CN | 107280665 A | 10/2017 |
| EP | 3229891 | 10/2017 |
| WO | 2016/205231 | 12/2016 |
| WO | 2018/008034 | 1/2018 |
| WO | 2018/163178 | 9/2018 |
| WO | 2018/213872 | 11/2018 |
| WO | 2019/070406 | 4/2019 |
| WO | 2019/210371 | 11/2019 |
| WO | 2019/211314 | 11/2019 |
| WO | 2019/217079 | 11/2019 |
| WO | 2020/223165 | 11/2020 |
| WO | 2021/026151 | 2/2021 |
| WO | 2021/080727 | 4/2021 |

OTHER PUBLICATIONS

International Search Report and Written Opinion regarding corresponding PCT Application No. PCT/US2023/077096, mailed Feb. 5, 2024.

Zelmann, Rina, et al., "Automatic Optimization of Depth Electrode Trajectory Planning," Montreal Neurological Institute Neurology and Neurosurgery, CLIP 2013, LNCS 8361, 2014, pp. 99-104.

Beriault, Silvain, et al., "A Multi-Modal Approach to Computer-Assisted Deep Brain Stimulation Trajectory Planning," International Journal of Computer Assisted Radiology and Surgery, 7, 2012, pp. 687-704.

Beriault, Silvain, et al., "A Prospective Evaluation of Computer-Assisted Deep Brain Stimulation Trajectory Planning," Montreal Neurological Institute McConnell Brain Imaging Centre, CLIP 2012, LNCS 7761, 2013, pp. 42-49.

Frankemolle, A.M.M., et al., "Reversing Cognitive-Motor Impairments in Parkinson's Disease Patients Using a Computational Modelling Approach to Deep Brain Stimulation Programming," Brain—A Journal of Neurology, 2010, 133, pp. 746-761.

Georgopoulos, Apostolos P., et al., "On the Relations Between the Direction of Two-Dimensional Arm Movements and Cell Discharge in Primate Motor Cortex," The Journal of Neuroscience, vol. 2, No. 11, pp. 1527-1537, 1982.

Gmel, Gerrit E., et al., "A New Biomarker for Closed-Loop Deep Brain Stimulation in the Subthalamic Nucleus for Patients with Parkinson's Disease," IEEE Biomedical Circuits and Systems Conference (BioCAS) Proceedings, Lausanne, 2014, pp. 500-503.

Gmel, Gerrit E., et al., "A New Biomarker for Subthalamic Deep Brain Stimulation for Patients with Advanced Parkinson's Disease—A Pilot Study," J. Neural Eng., 12, 2015, 11 pages.

Gmel, Gerrit Eduard, "Evoked Brain Neural Potentials," Dissertation for The University of New South Wales, Sep. 2016, 231 pages.

Hatsopoulos, Nicholas G et al., "Sensing with the Motor Cortex," J. Neuron, 72(3), 22 pages, 2011.

Kent, A.R., et al., "Recording Evoked Potentials During Deep Brain Stimulaton: Development and Validation of Instrumentation to Suppress to Stimulus Artefact," J Neural Eng., 9(3), Jun. 2012, 30 pages.

Kent, Alexander R., et al., "Neural Origin of Evoked Potentials During Thalamic Deep Brain Stimulation," J Neurophysiol, 110, 2013, pp. 826-843.

Kent, Alexander Rafael, et al., "Characterization of Evoked Potentials During Deep Brain Stimulation in the Thalamus," Dissertation Submitted in the Department of Biomedical Engineering Duke University, 2013, 320 pages.

Kirsch AD, et al., "Anodic Versus Cathodic Neurostimulation of the Subthalamic Nucleus: A Randomized-Controlled Study of Acute Clinical Effects," Parkinsonism and Related Disorders, 55, 2018, pp. 61-67.

Laarne, Paivi, et al., "Accuracy of Two Dipolar Inverse Algorithms Applying Reciprocity for Forward Calculation," Computers and Biomedical Research, vol. 33, Issue 3, pp. 172-185, Jun. 2000.

Moffitt, Michael A., et al., "Electrical Localization of Neural Activity in the Dorsal Horn of the Spinal Cord: A Modeling Study," Annals of Biomedical Engineering, 32(12), pp. 1694-1709, 2004.

Pascual-Marqui, RD, "Standardized Low-Resolution Brain Electromagnetic Tomography (sLORETA): Technical Details," Methods Find Exp Clin Pharmacol, 24 Suppl D, 5-12. 2002.

Shils, Jay, et al., "Motor Evoked Potential Recordings During Segmented DBS—A Feasibility Study," Oper Neurosurg (Hagerstown), Mar. 15, 2021, 20(4), pp. 419-425.

Sinclair, Nicholas C., et al., "Deep Brain Stimulation for Parkinson's Disease Modulates High-Frequency Evoked and Spontaneous Neural Activity," Neurobiology of Disease, vol. 130, 104522, Oct. 2019.

Sinclair, Nicholas C., et al., "Directional Deep Brain Stimulation Evoked Resonant Neural Activity (ERNA)," Poster, 2020, 1 page.

Sinclair, Nicholas C., et al., "On the Neural Basis of Deep Brain Stimulation Evoked Resonant Activity," Biomed. Phys. Eng. Express, 5, 2019, 9 pages.

Sinclair, Nicholas C., et al., "Subthalamic Nucleus Deep Brain Stimulation Evokes Resonant Neural Activity," Annals of Neurology, 83(5), pp. 1027-1031, May 4, 2018.

Sinclair, Nicholas C., et al., "Subthalamic Nucleus Deep Brain Stimulation Evokes Resonant Neural Activity," Poster, 2019, 1 page.

Thevathasan, Wesley, et al., "Tailoring Subthalamic Nucleus Deep Brain Stimulation for Parkinson's Disease Using Evoked Resonant Neural Activity," Frontiers in Human Neuroscience, vol. 14, Article 71, Feb. 2020, 6 pages.

Walker, Harrison, MD, et al., Directional Subthalamic Nucleus DBS for Parkinson's Disease: Year 3 Interim Analyses, UAB Medicine Poster, 2020, 1 page.

Wiest, C. et al., "Local Field Potential Activity Dynamics in Response to Deep Brain Stimulation of the Subthalamic Nucleus in Parkinson's Disease," Neurobiology of Disease, 143, 2020, 15 pages.

Wiest, C., et al., "Subthalamic Deep Brain Stimulation Induces Finely-Tuned Gamma Oscillations in the Absence of Levodopa," Neurobiology of Disease, 152, 105287, 2021, 13 pages.

Wiest, C., et al., "Local Field Potential Activity Dynamics in Response to Deep Brain Stimulation of the Subthalamic Nucleus in Parkinson's Disease." Neurobiology of Disease, 2019, 41 pages.

* cited by examiner

E2: 18%(-I)

E4: 52%(-I)

E5: 8%(-I)

E7: 22%(-I)

Ec: 100*(+I)

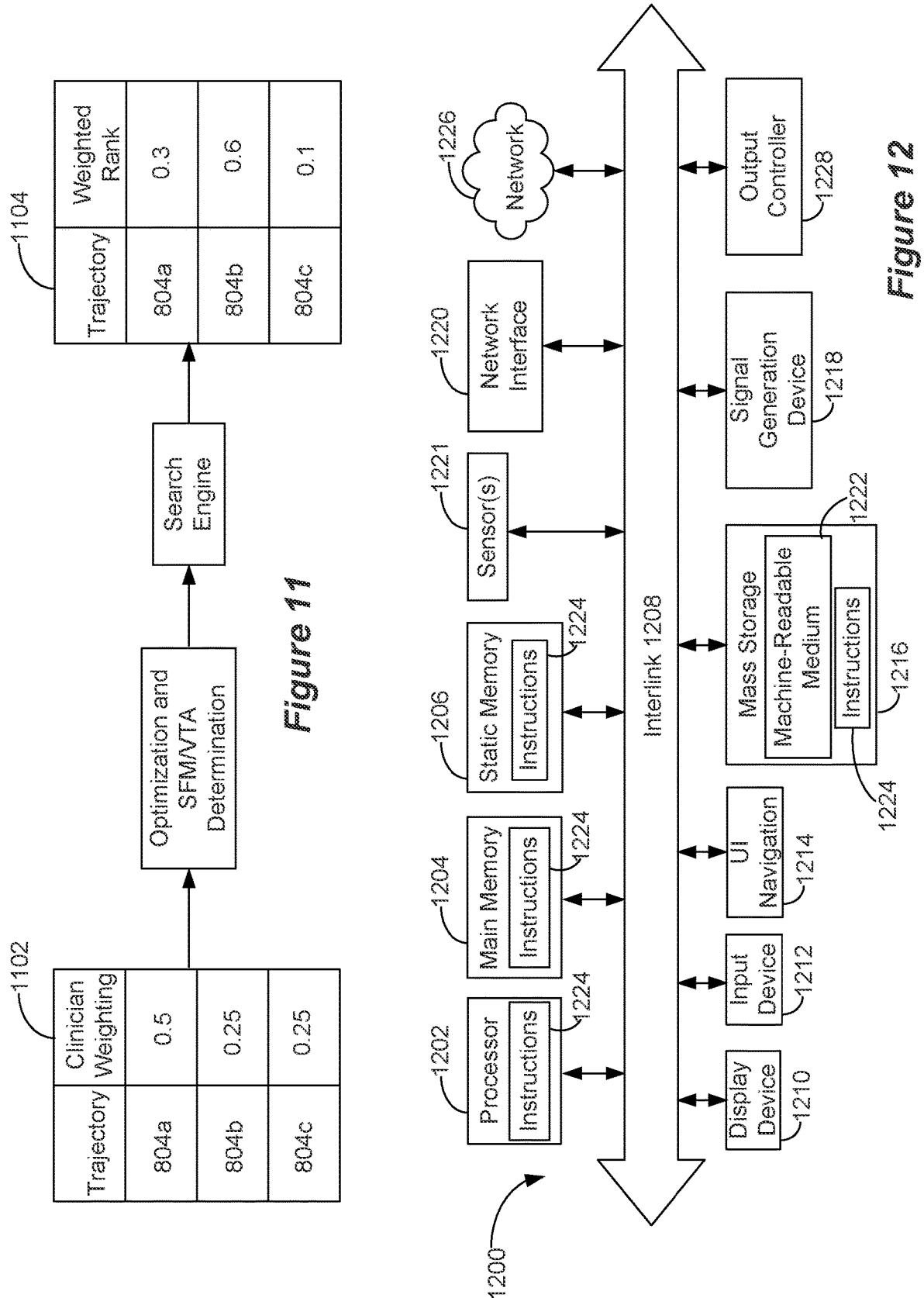

Figure 11

| Trajectory | Clinician Weighting |
|---|---|
| 804a | 0.5 |
| 804b | 0.25 |
| 804c | 0.25 |

1102

Optimization and SFM/VTA Determination

Search Engine

| Trajectory | Weighted Rank |
|---|---|
| 804a | 0.3 |
| 804b | 0.6 |
| 804c | 0.1 |

Interlink 1208

Processor 1202 — Instructions 1224

Main Memory 1204 — Instructions 1224

Static Memory 1206 — Instructions 1224

Sensor(s) 1221

Network Interface 1220

Network 1226

Display Device 1210

Input Device 1212

UI Navigation 1214

Mass Storage 1216 — Machine-Readable Medium 1222 — Instructions 1224

Signal Generation Device 1218

Output Controller 1228

NEUROANATOMY-BASED SEARCH TO OPTIMIZE TRAJECTORY SELECTION DURING DBS TARGETING

CROSS REFERENCE TO RELATED APPLICATIONS

This is a non-provisional application of U.S. Provisional Patent Application Ser. No. 63/380,099, filed Oct. 19, 2022, which is incorporated herein by reference in its entirety, and to which priority is claimed.

FIELD OF THE INVENTION

This application relates to Implantable Stimulator Devices (ISD), and more specifically to an algorithm and system for selecting trajectory selection in an ISD such as a Deep Brain Stimulation (DBS) device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS) system, such as that disclosed in U.S. Patent Application Publication 2020/0001091, which is incorporated herein by reference. However, the present invention may find applicability with any implantable neurostimulator device system, including Spinal Cord Stimulation (SCS) systems, Vagus Nerve Stimulation (VNS) system, Sacral Nerve Stimulation (SNS) systems, Peripheral Nerve Stimulation (PNS) systems, and the like.

A DBS system typically includes an Implantable Pulse Generator (IPG) 10 shown in FIG. 1A. The IPG 10 includes a biocompatible device case 12 that holds the circuitry and a battery 14 for providing power for the IPG to function, although the IPG 10 can also lack a battery and can be wirelessly powered by an external source. The IPG 10 is coupled to tissue-stimulating electrodes 16 via one or more electrode leads 18 or 19, which are shown in more details in FIGS. 1B and 1C.

FIG. 1B shows a lead 18 having eight ring-shaped electrodes 16 which are located at different longitudinal positions along a central axis 15. Lead 18 is referred to herein as a "non-directional lead," because the ring-shaped electrodes span 360 degrees around the axis 15, and thus cannot direct stimulation to different rotational positions around the axis 15.

FIG. 1C shows a lead 19 also having eight electrodes, but not all of the electrodes are ring-shaped. Electrode E8 at the distal end of the lead 19 and electrode E1 at a proximal end of the lead are ring-shaped. Electrodes E2, E3, and E4, by contrast, comprise split-ring electrodes, each of which are located at the same longitudinal position along the axis 15, but each spanning less than 360 degrees around the axis. For example, each of electrodes E2, E3, and E4 may span 90 degrees around the axis 15, with each being separated from the others by gaps of 30 degrees. Electrodes E5, E6, and E7 also comprise split-ring electrodes, but are located at a different longitudinal position. Lead 19 is referred to herein as a "directional lead," because at least some of the electrodes at a given longitudinal position (e.g., E2, E3, E4) span less than 360 degrees, meaning that those electrodes can direct stimulation to different rotational positions (and hence different brain tissues) around the axis 15. In other designs of a directional lead 19, all electrodes can be split-ring, or there could be different numbers of split-ring electrodes at each longitudinal position (i.e., more or less than three).

Lead wires 20 within the leads are coupled to the electrodes 16 and to proximal contacts 21 insertable into lead connectors 22 fixed in a header 23 on the IPG 10, which header can comprise an epoxy for example. Alternatively, the proximal contacts 21 may connect to lead extensions (not shown) which are in turn inserted into the lead connectors 22. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the IPG 10 illustrated in FIG. 1A, there are thirty-two electrodes (E1-E32), split between four percutaneous leads 18 or 19 (18 is shown), and thus the header 23 may include a 2×2 array of eight-electrode lead connectors 22. However, the type and number of leads, and the number of electrodes, in an IPG is application specific and therefore can vary. In another example not shown, a given lead can have 16 sixteen electrodes, and thus this lead would have two sets of proximal contacts 21 to mate with two of the eight-electrode lead connectors 22, as disclosed for example in U.S. Patent Application Publication 2019/0076645. The conductive case 12 can also comprise an electrode (Ec).

In a DBS application, as is useful in the treatment of tremor in Parkinson's disease for example, the IPG 10 is typically implanted under the patient's clavicle (collarbone). Leads 18 or 19 (perhaps as extended by lead extensions, not shown) are tunneled through and under the neck and the scalp, with the electrodes 16 implanted through holes drilled in the skull and positioned in the brain. The IPG 10 can also be implanted underneath the scalp closer to the location of the electrodes' implantation, as disclosed for example in U.S. Pat. No. 10,576,292. The IPG lead(s) 18 or 19 can be integrated with and permanently connected to the IPG 10 in other solutions.

IPG 10 can include an antenna 27a allowing it to communicate bi-directionally with a number of external devices and systems discussed subsequently. Antenna 27a as shown comprises a conductive coil within the case 12, although the coil antenna 27a can also appear in the header 23. When antenna 27a is configured as a coil, communication with external systems preferably occurs using near-field magnetic induction. IPG 10 may also include a Radio-Frequency (RF) antenna 27b. In FIG. 1A, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, WiFi, MICS, and the like. If the IPG 10 lacks a battery 14, an additional coil can be present to receive wireless power from an external source.

Stimulation in IPG 10 is typically provided by pulses each of which may include a number of phases such as 30a and 30b, as shown in the example of FIGS. 2A and 2B. In the example shown, such stimulation is monopolar, meaning that a current is provided between at least one selected lead-based electrode (e.g., E1) and the case electrode Ec 12. Stimulation could be bipolar, in which a current is provided between at least two lead-based electrodes, as shown, or may be monopolar. Stimulation parameters typically include amplitude (current I, although a voltage amplitude V can also be used); frequency (F); pulse width (PW) of the pulses or of its individual phases such as 30a and 30b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as a cathode (during its first phase 30a), and thus provides pulses which sink a negative current of amplitude −I from the tissue. The case electrode Ec has been selected as an anode (again during first phase 30a), and thus provides pulses which source a corresponding positive current of amplitude +I to the tissue. Note that at any time the current sunk from the tissue (e.g., −I at E1 during phase 30a) equals the current sourced to the tissue (e.g., +I at Ec during phase 30a). The polarity of the currents at these electrodes can be changed: for example, during first phase 30a, Ec can be selected as a cathode, and E1 can be selected as an anode, etc. Monophasic stimulation may also be used.

IPG 10 as mentioned includes stimulation circuitry 28 to form prescribed stimulation at a patient's tissue. FIG. 3 shows an example of stimulation circuitry 28, which includes one or more current sources $40_i$ and one or more current sinks $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. PDACs $40_i$ and NDACs $42_i$ can also comprise voltage sources.

Proper control of the PDACs $40_i$ and NDACs $42_i$ allows any of the electrodes 16 and the case electrode Ec 12 to act as anodes or cathodes to create a current (such as the pulses described earlier) through a patient's tissue, Z, hopefully with good therapeutic effect. In the example shown, and consistent with the first pulse phase 30a of FIG. 2A, electrode E1 has been selected as a cathode electrode to sink current from the tissue Z and case electrode Ec has been selected as an anode electrode to source current to the tissue Z. Thus PDAC $40_C$ and NDAC $42_1$ are activated and digitally programmed to produce the desired current, I, with the correct timing (e.g., in accordance with the prescribed frequency F and pulse width PW). Power for the stimulation circuitry 28 is provided by a compliance voltage VH, as described in further detail in U.S. Patent Application Publication 2013/0289665. Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606, 362, 8,620,436, U.S. Patent Application Publications 2018/0071520 and 2019/0083796.

Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas 27a and/or 27b), circuitry for generating the compliance voltage VH, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Referring again to FIG. 2A, the stimulation pulses as shown are biphasic, with each pulse comprising a first phase 30a followed thereafter by a second phase 30b of opposite polarity. Biphasic pulses are useful to actively recover any charge that might be stored on capacitive elements in the electrode current paths, such as on the DC-blocking capacitors 38, as is well known. FIG. 3 also shows that stimulation circuitry 28 can include passive recovery switches $41_i$, which are described further in U.S. Patent Application Publications 2018/0071527 and 2018/0140831. Passive recovery switches $41_i$ may be closed to passively recover any charge remaining on the DC-blocking capacitors Ci 38 after issuance of the second pulse phase 30b—i.e., to recover charge without actively driving a current using the DAC circuitry, as shown during duration 30c. Alternatively, passive charge recovery can be used during the second pulse phase 30b after the actively driven first pulse phase 30a, although this isn't shown in FIG. 2A. Again, passive charge recovery is well known and not further described.

FIG. 4 shows various external systems 60, 70, and 80 that can wirelessly communicate data with the IPG 10. Such systems can be used to wirelessly transmit a stimulation program to the IPG 10—that is, to program its stimulation circuitry 28 to produce stimulation with desired amplitudes and timings as described earlier. Such systems may also be used to adjust one or more stimulation parameters of a stimulation program that the IPG 10 is currently executing, and/or to wirelessly receive information from the IPG 10, such as various status information and measurements, etc.

External controller 60 can be as described in U.S. Patent Application Publication 2015/0080982 for example, and may comprise a portable, hand-held controller dedicated to work with the IPG 10. External controller 60 may also comprise a general-purpose mobile electronics device such as a mobile phone which has been programmed with a Medical Device Application (MDA) allowing it to work as a wireless controller for the IPG 10, as described in U.S. Patent Application Publication 2015/0231402. External controller 60 includes a display 61 and a means for entering commands, such as buttons 62 or selectable graphical icons provided on the display 61. The external controller 60's user interface enables a patient to adjust stimulation parameters, although it may have limited functionality when compared to systems 70 and 80, described shortly. The external controller 60 can have one or more antennas capable of communicating with a compatible antenna in the IPG 10, such as a near-field magnetic-induction coil antenna 64a and/or a far-field RF antenna 64b.

Clinician programmer 70 is described further in U.S. Patent Application Publication 2015/0360038, and can comprise a computing device such as a desktop, laptop, or notebook computer, a tablet, a mobile smart phone, a Personal Data Assistant (PDA)-type mobile computing device, etc. In FIG. 4, the computing device is shown as a laptop computer that includes typical computer user interface means such as a display 71, buttons 72, as well as other user-interface devices such as a mouse, a keyboard, speakers, a stylus, a printer, etc., not all of which are shown for convenience. Also shown in FIG. 4 are accessory devices for the clinician programmer 70 that are usually specific to its operation as a stimulation controller. A communication "wand" 76 couplable to suitable ports on the computing device can include an IPG-compliant antenna such as a coil antenna 74a or an RF antenna 74b. The computing device itself may also include one or more RF antenna 74b. The clinician programmer 70 can also communicate with other devices and networks, such as the Internet, either wirelessly or via a wired link provided at an Ethernet or network port.

External system 80 comprises another means of communicating with and controlling the IPG 10 via a network 85 which can include the Internet. The network 85 can include a server 86 programmed with IPG communication and control functionality, and may include other communication networks or links such as WiFi, cellular or land-line phone links, etc. The network 85 ultimately connects to an intermediary device 82 having antennas suitable for communication with the IPG's antenna, such as a near-field magnetic-induction coil antenna 84a and/or a far-field RF antenna 84b. Intermediary device 82 may be located generally proximate to the IPG 10. Network 85 can be accessed by any user terminal 87, which typically comprises a computer device associated with a display 88. External system 80 allows a remote user at terminal 87 to communicate with and control the IPG 10 via the intermediary device 82.

FIG. 4 also shows circuitry 90 involved in any of external systems 60, 70, or 80. Such circuitry can include control circuitry 92, which can comprise any number of devices such as one or more microprocessors, microcomputers, FPGAs, DSPs, other digital logic structures, etc., which are capable of executing programs in a computing device. Such control circuitry 92 may contain or coupled with memory 94 which can store external system software 96 for controlling and communicating with the IPG 10, and for rendering a Graphical User Interface (GUI) 99 on a display (61, 71, 88) associated with the external system. In external system 80, the external system software 96 would likely reside in the server 86, while the control circuitry 92 could be present in either or both the server 86 or the terminal 87.

FIG. 5A shows an example of GUI 99 renderable on the display of an external system, such as the clinician programmer 70 mentioned earlier. GUI 99 is particularly useful in an DBS context because it provides a clinician with a visual indication of how stimulation selected for a patient will interact with the brain tissue in which the electrodes are implanted. GUI 99 can be used during surgical implantation of the leads 18 or 19 and its IPG 10, but can also be used after implantation to assist in selecting a therapeutically useful stimulation program for the patient. The GUI 99 can be controlled by a cursor 101 that the user can move using a mouse connected to the clinician programmer 70 for example.

The GUI 99 may include a waveform interface 104 where various aspects of the stimulation can be selected or adjusted. For example, waveform interface 104 allows a user to select an amplitude (e.g., a current I), a frequency (F), and a pulse width (PW) of the stimulation pulses. Waveform interface 104 can be significantly more complicated, particularly if the IPG 10 supports the provision of stimulation that is more complicated than a repeating sequence of pulses. Waveform interface 104 may also include inputs to allow a user to select whether stimulation will be provided using biphasic (FIG. 2A) or monophasic pulses, or in bursts of pulses, and to select whether passive charge recovery will be used, although again these details aren't shown for simplicity.

The GUI 99 may also include an electrode configuration interface 105 which allows the user to select a particular electrode configuration specifying which electrodes should be active to provide the stimulation, and with which polarities and relative magnitudes. In this example, the electrode configuration interface 105 allows the user to select whether an electrode should comprise an anode (A) or cathode (C) or be off, and allows the amount of the total anodic or cathodic current +I or −I (specified in the waveform interface 104) that each selected electrode will receive to be specified in terms of a percentage, X. For example, in FIG. 5A, the case electrode 12 Ec is specified to be an anode that receives X=100% of the current I as an anodic current +I (e.g., during first pulse phase 30a if biphasic pulses are used; see FIG. 2A). The corresponding cathodic current −I is split between cathodes electrodes E2 (18% or 0.18*−I), E4 (52% or 0.52*−I), E5 (8% or 0.08*−I), and E7 (22% or 0.22*−I) (again during first pulse phase 30a). The waveforms resulting at the electrodes from this electrode configuration are shown in FIG. 5B. Note that two or more electrodes can be chosen to act as anodes or cathodes at a given time, allowing the electric field in the tissue to be shaped, as explained further below. Once the waveform parameters (104) and electrode configuration parameters (105) are determined, they can be sent from the clinician programmer 70 to the IPG 10, so that the IPG's stimulation circuitry 28 (FIG. 3) can be programmed (the various NDACs and PDACs) to produce the desired currents at the selected electrodes with the proper timing. For example, PDAC 40c would be programmed to produce +100%*+I, and NDAC 42₄ would be programmed to produce 52%*−I, etc. Together, the various waveform parameters and electrode configuration parameter comprise stimulation parameters, which together comprise a stimulation program.

Use of these electrodes to provide cathodic stimulation sets a particular position for a cathodic pole 120 in three-dimensional space. The position of this cathode pole 120 can be quantified at a particular longitudinal position L along the lead (e.g., relative to a point on the lead such as the longitudinal position of electrode E1), and at a particular rotational angle θ (e.g., relative to a particular angle on the lead such as relative to the center of electrode E2). (Note that rotation angle θ is only relevant when a directional lead such as 19 (FIG. 1C) is used). This position is shown in a leads interface 102 of the GUI 99. Notice that the position of the pole 120 (L,θ) may be virtual; that is, the position may not necessarily occur at the physical position of any of the electrodes 16 in the electrode array, as explained further later. The leads interface 102 preferably also includes an image 103 of the lead being used for the patient. Although not shown, the leads interface 102 can include a selection to access a library of relevant representations 103 of the types of leads (e.g., 18 or 19) that may be implanted in different patients, which may be stored with the relevant software (e.g., 96, FIG. 4). The cursor 101 can be used to select an illustrated electrode 16 (e.g., E1-E8, or the case electrode Ec), or a pole such as cathode pole 120. Pole 120 could also be anodic, or there could be more than one pole if multipolar stimulation is used, but this isn't shown.

An electrode configuration algorithm (not shown), operating as part of external device's software 96, can determine a position of the cathode pole 120 in three-dimensional space from a given electrode configuration, and can also conversely determine an electrode configuration from a given position of the pole 120. For example, the user can place the position of the pole 120 using the cursor 101. The electrode configuration algorithm can then be used to compute an electrode configuration that best places the pole 120 in this position. Note that cathode pole 120 is positioned closest to electrode E4, but is also generally proximate to electrodes E2, E7, and E6. The electrode configuration algorithm may thus calculate that electrode E4 should receive the largest share of cathodic current (52%*–I), while E2, E7, and E6 which are farther away from the pole 120 receive lesser percentages, as shown in the stimulation parameters interface 104. By involving more than one electrode, cathode pole 120 is formed as a virtual pole not as the position of any of the physical electrodes. Again, the electrode configuration algorithm can also operate in reverse: from a given electrode configuration, the position of the pole 120 can be determined. The electrode configuration algorithm is described further in U.S. Patent Application Publication 2019/0175915, which is incorporated herein by reference.

GUI 99 can further include a visualization interface 106 that allows a user to view a stimulation field image 112 formed on a lead given the selected stimulation parameters and electrode configuration. The stimulation field image 112 is formed by field modelling in the clinician programmer 70, as discussed further in the '091 Publication. The visualization interface 106 preferably, but not necessarily, further includes tissue imaging information 114. This tissue imaging information 114 is presented in FIG. 5A as three different tissue structures 114a, 114b and 114c in FIG. 6 for the patient in question, which tissue structures may comprise different areas of the brain for example. Such tissue imaging information may come from a Magnetic Resonance Image (MRI) or Computed Tomography (CT) image of the patient, any structural or functional imaging modality, it may come from a generic library of images, and may include user defined regions. The GUI 99 can overlay the lead image 111 and the stimulation field image 112 with the tissue imaging information 114 in the visualization interface 106 so that the position of the stimulation field 112 relative to the various tissue structures 114i can be visualized. The various images shown in the visualization interface 106 (i.e., the lead image 111, the stimulation field image 112, and the tissue structures 114i) can be three-dimensional in nature, and hence may be rendered to allow such three-dimensionality to be better appreciated by the user, such as by shading or coloring the images, etc. A view adjustment interface 107 may allow the user to move or rotate the images, using cursor 101 for example, as explained in the '091 Publication. In FIG. 5A, a cross-section interface 108 allows the various images to be seen in a particular two-dimensional cross section, and in this example a cross section 109 is shown taken perpendicularly to the lead image 111 and through split-ring electrodes E2, E3, and E4. Interfaces 106 and 108 may also show the cathode pole 120 in a proper position, but this isn't shown.

The GUI 99 of FIG. 5A is particularly useful because it allows the electric field as reflected in stimulation field image 112 (or the pole 120) to be seen relative to surrounding tissue structures 114i. This allows the user to adjust the stimulation parameters to recruit, or avoid recruiting, particular tissue structures 114i. Assume for example that it is desirable for a given patient to stimulate tissue structure 114a, but to not stimulate tissue structures 114b or 114c. This may be because tissue structure 114a is causing undesired patient symptoms (e.g., tremor) that stimulation can alleviate, while stimulation of tissue structures 114b and 114c will cause undesired side effects. The clinician can then use GUI 99 to adjust stimulation (e.g., to adjust the stimulation parameters or the electrode configuration) to move the stimulation field 112 (e.g., the cathode pole 120) to a proper position (L, θ). In the example shown, and as best seen in the cross-section interface 108, higher cathodic currents are provided at split-ring electrodes E4 (0.52*–I) and E2 (0.18*–I) because these electrodes are generally facing towards tissue structure 114a which should be stimulated. By contrast, split-ring electrode E3 carries no cathodic current because it generally faces towards tissue structure 114b where stimulation is ideally avoided. The result is a stimulation field 112 that is more predominant in tissue structure 114a and less predominant in tissue structure 114b, as shown in the visualization interface 106.

Especially in a DBS application, it is important that correct stimulation parameters be determined for a given patient. Improper stimulation parameters may not yield effective relief of a patient's symptoms, or may cause unknown or unwanted side effects. To determine proper stimulation, a clinician typically uses GUI 99 to try different combinations of stimulation parameters. This may occur, at least in part, during a DBS patient's surgery when the leads are being implanted. Such intra-operative determination of stimulation parameters can be useful to determine a general efficacy of DB S therapy and to confirm lead placement. However, finalizing stimulation parameters that are appropriate for a given DBS patient typically occurs after surgery after the patient has had a chance to heal, and after the position of the leads stabilize in the patient. Thus, at such time, the patient will typically present to the clinician's office to determine (or further refine) optimal stimulation parameters during a programming session.

A DBS procedure typically involves first obtaining pre-operative images of the patient's brain, such as by using a computed tomography (CT) scanner device, a magnetic resonance imaging (MRI) device, or any other imaging modality. This sometimes involves first affixing to the patient's skull spherical or other fiducial markers that are visible on the images produced by the imaging modality. The fiducial markers help register the preoperative images to the actual physical position of the patient in the operating room during the later surgical procedure.

After the preoperative images are acquired by the imaging modality, they are then loaded onto an image-guided surgical (IGS) workstation. Using the preoperative images being displayed on the IGS workstation, a neurosurgeon can select a target region within the brain, an entry point on the patient's skull, and a desired trajectory between the entry point and the target region. The entry point and trajectory are typically carefully selected to avoid intersecting or otherwise damaging certain nearby critical brain structures or vasculature.

In the operating room, the patient is immobilized and the patient's actual physical position is registered to the preoperative images displayed on the IGS workstation, such as by using a remotely detectable IGS wand. In one example, the physician marks the entry point on the patient's skull, drills a burr hole at that location, and affixes a trajectory guide device about the burr hole. The trajectory guide device includes a bore that can be aimed using the IGS wand to obtain the desired trajectory to the target region. After aiming, the trajectory guide is locked to preserve the aimed trajectory toward the target region. After the aimed trajectory has been locked in using the trajectory guide, a microdrive introducer is used to insert the surgical instrument along the trajectory toward the target region of the brain. The trajectory may be refined (often on the fly) during the electrode implantation.

There is a need in the art for methods and systems for aiding the clinician during the planning stage to determine lead trajectories that have the highest chance of achieving therapeutic goals or that meet other criteria that the clinician deems important.

SUMMARY

Disclosed herein is a method for planning a position for a stimulation lead for neurostimulation of one or more target structures of a patient's brain, wherein the stimulation lead comprises a tip, a longitudinal axis, and a plurality of electrode contacts, the method comprising: determining a plurality of candidate positions for the stimulation lead; determining a set of optimized stimulation parameters for each of the candidate positions; predicting a volume of tissue activated (VTA) for each of the candidate positions' set of optimized stimulation parameters; determining an overlap of each of the predicted VTA with the target structure, and ranking the plurality of candidate positions based at least partially on the overlaps. According to some embodiments, the method further comprises implanting the stimulation lead in the patient's brain according to the highest ranked candidate position. According to some embodiments, each candidate position is defined by a tip location, a rotation angle, and a longitudinal axis angle. According to some embodiments, the indication of a plurality of candidate positions comprises an indication of a basis position and of values for one or more of the tip location, rotation angle, and/or longitudinal axis angle. According to some embodiments, determining a set of optimized stimulation parameters comprises using a reverse programming algorithm. According to some embodiments, the reverse programming algorithm comprises optimizing current fractionalization among the electrode contacts based on stimulation field models (SFMs) modeled for each current fractionalization. According to some embodiments, the reverse programming algorithm comprises optimizing one or more parameters selected from the group consisting of pulse-width, frequency and amplitude. According to some embodiments, the reverse programming algorithm comprises a cost function that includes (i) overlap of the SFMs with the target structure for each current fractionalization, and (ii) a cost associated with increasing a size of the SFM. According to some embodiments, the cost function is further a function of (iii) overlap of the SFMs with an avoidance structure for each current fractionalization. According to some embodiments, ranking the plurality of candidate positions is further based on one or more bounding parameters or additional scoring functions. According to some embodiments, the bounding parameters comprise maximum power usage. According to some embodiments, the bounding parameters specify one or more of stimulation amplitude values, total charge values, pulse width, or frequency. According to some embodiments, the method further comprises receiving an a priori ranking for each of the candidate positions, wherein the ranking of the plurality of candidate positions is further based on the a priori rankings.

Also disclosed herein is an apparatus for planning a position for a stimulation lead for neurostimulation of one or more target structures of a patient's brain, wherein the stimulation lead comprises a tip, a longitudinal axis, and a plurality of electrode contacts, the apparatus comprising: a processor configured to: receive an indication of a plurality of candidate positions for the stimulation lead; determine a set of optimized stimulation parameters for each of the candidate positions; predict a volume of tissue activated (VTA) for each of the candidate positions' set of optimized stimulation parameters; determine an overlap of each of the predicted VTA with the target structure, and rank the plurality of candidate positions based at least partially on the overlaps. According to some embodiments, each candidate position is defined by a tip location, a rotation angle, and a longitudinal axis angle. According to some embodiments, the indication of a plurality of candidate positions comprises an indication of a basis position and of values for one or more of the tip location, rotation angle, and/or longitudinal axis angle. According to some embodiments, determining a set of optimized stimulation parameters comprises using a reverse programming algorithm. According to some embodiments, the reverse programming algorithm comprises optimizing current fractionalization among the electrode contacts based on stimulation field models (SFMs) modeled for each current fractionalization. According to some embodiments, the reverse programming algorithm comprises optimizing one or more parameters selected from the group consisting of pulse-width, frequency and amplitude. According to some embodiments, the reverse programming algorithm comprises a cost function that includes (i) overlap of the SFMs with the target structure for each current fractionalization, and (ii) a cost associated with increasing a size of the SFM. According to some embodiments, the cost function is further a function of (iii) overlap of the SFMs with an avoidance structure for each current fractionalization. According to some embodiments, ranking the plurality of candidate positions is further based on one or more bounding parameters. According to some embodiments, the bounding parameters comprise maximum power usage. According to some embodiments, the bounding parameters specify one or more of stimulation amplitude values, total charge values, pulse width, or frequency. According to some embodiments, the processor is further configured to receive an a priori ranking for each of the candidate positions, wherein the ranking of the plurality of candidate positions is further based on the a priori rankings.

Also disclosed herein is a for planning a position for a stimulation lead for neurostimulation of one or more target structures of a patient's brain, wherein the stimulation lead comprises a tip, a longitudinal axis, and a plurality of electrode contacts, the method comprising: receiving an indication of a plurality of candidate positions for the stimulation lead; determining a set of optimized stimulation parameters for each of the candidate positions; for each of the candidate positions, predicting a therapeutic effect using that candidate positions' optimized stimulation parameters, and ranking the plurality of candidate positions based at least partially on the predicted therapeutic effect. According to some embodiments, the therapeutic efficacy comprises an extent to which the candidate positions' optimized stimulation parameters will stimulate the one or more target structures. According to some embodiments, the therapeutic effect comprises an extent to which the candidate positions' optimized stimulation parameters will avoid stimulating one or more non-target structures.

Also disclosed herein is an apparatus for planning a position for a stimulation lead for neurostimulation of one or more target structures of a patient's brain, wherein the stimulation lead comprises a tip, a longitudinal axis, and a plurality of electrode contacts, the apparatus comprising: control circuitry configured to: receive an indication of a plurality of candidate positions for the stimulation lead; determine a set of optimized stimulation parameters for each of the candidate positions; for each of the candidate positions, predict a therapeutic effect using that candidate positions' optimized stimulation parameters, and rank the plurality of candidate positions based at least partially on the predicted therapeutic effect. According to some embodiments, the therapeutic efficacy comprises an extent to which the candidate positions' optimized stimulation parameters will stimulate the one or more target structures. According to some embodiments, the therapeutic effect comprises an extent to which the candidate positions' optimized stimulation parameters will avoid stimulating one or more non-target structures.

The invention may also reside in one or more non-volatile computer readable memories comprising instructions that, when executed by a processor, configure the processor to perform any of the methods described above.

BRIEF DESCRIPTION OF THE DRAWINGS

FIG. 11 shows sorting and weighting of candidate lead trajectories.

FIG. 12 shows a machine configured for selecting a lead trajectory.

DETAILED DESCRIPTION

Figures 5B, 6:
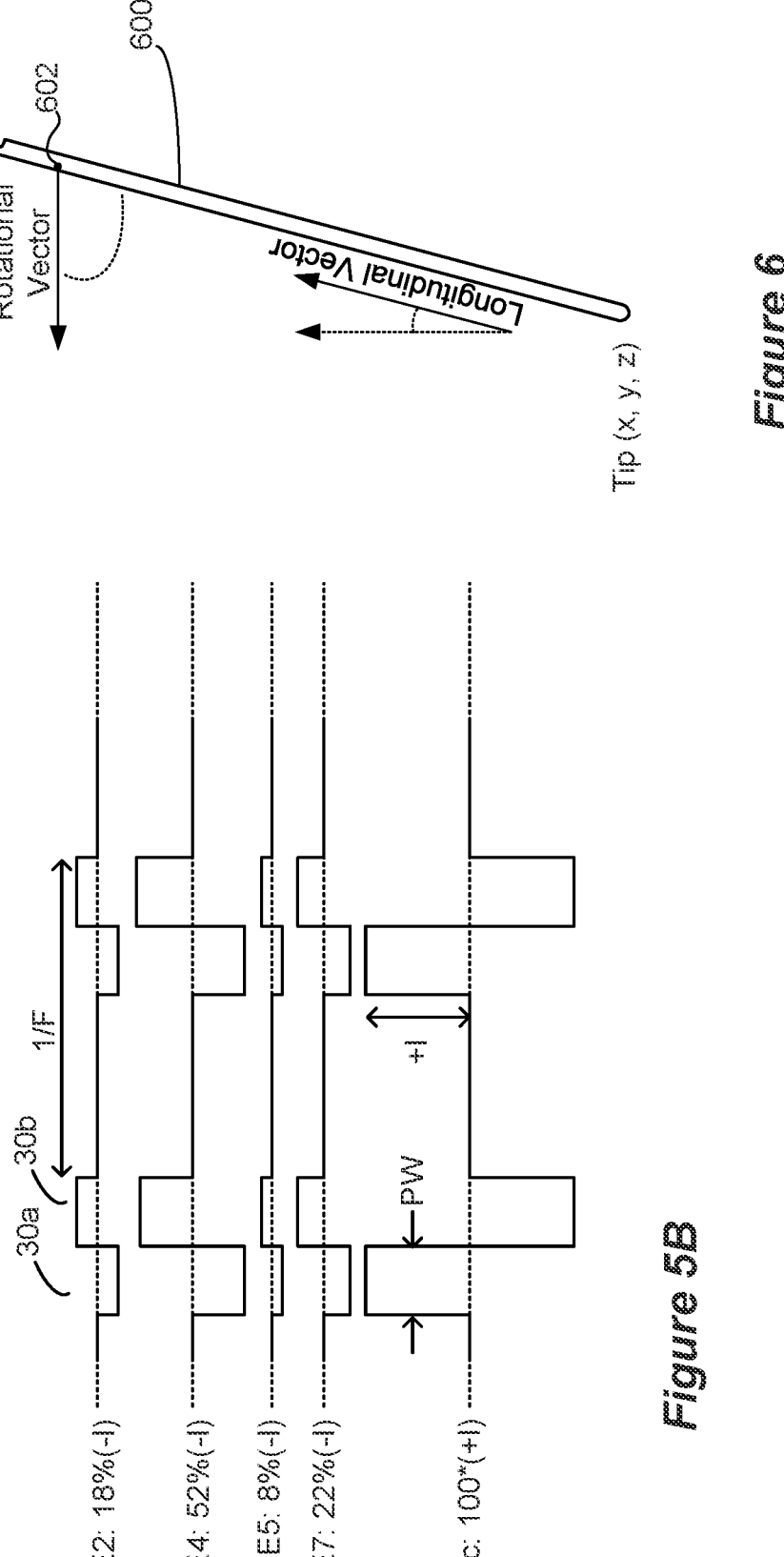
FIG. 5B shows waveforms produced at the electrodes through use of the GUI of FIG. 5A.
FIG. 6 shows an embodiment of how an electrode lead's trajectory may be defined.

As mentioned above, prior to implanting DBS leads into a patient's brain, the surgeon will first plan trajectories for the leads. As used herein, the term "trajectory" refers to the position and orientation of the DBS lead(s), often including an entry-point on the surface of the brain to some target point within. FIG. 6 illustrates information that may define the trajectory of a lead 600. The lead's trajectory may be defined by (1) the position of the lead tip (e.g., x, y, z coordinates), (2) a longitudinal vector that describes the shaft of the lead 600, extending from the tip toward the distal end of the lead, and (3) a rotational vector that is orthogonal to the longitudinal vector and that describes the rotation of a marker 602. Generally, the surgeon may try to implant the lead so that the marker faces a consistent direction, such as anteriorly, but the lead may be rotated intentionally or during the course of implant.

The surgeon may use preoperative imaging to determine trajectories that the surgeon believes have the highest chance for allowing successful therapeutic stimulation, while considering factors, such as avoiding vasculature, critical brain structures, and the like. A challenge during the planning stage is that the only planning information the surgeon has available is anatomical information, i.e., the imaging data, etc. They do not know what types of stimulation programs they may be able to activate with any particular trajectory, the volume of tissue activation they may achieve, the stimulation fields they may obtain, etc. For example, the trajectory may be designed to locate the electrode lead within or proximate to a desired neural structure, but the physician may still not be sure that they will be able to determine a stimulation program that will provide a stimulation field that adequately or optimally activates the desired neural target.

Figures 7, 8A, 8B:
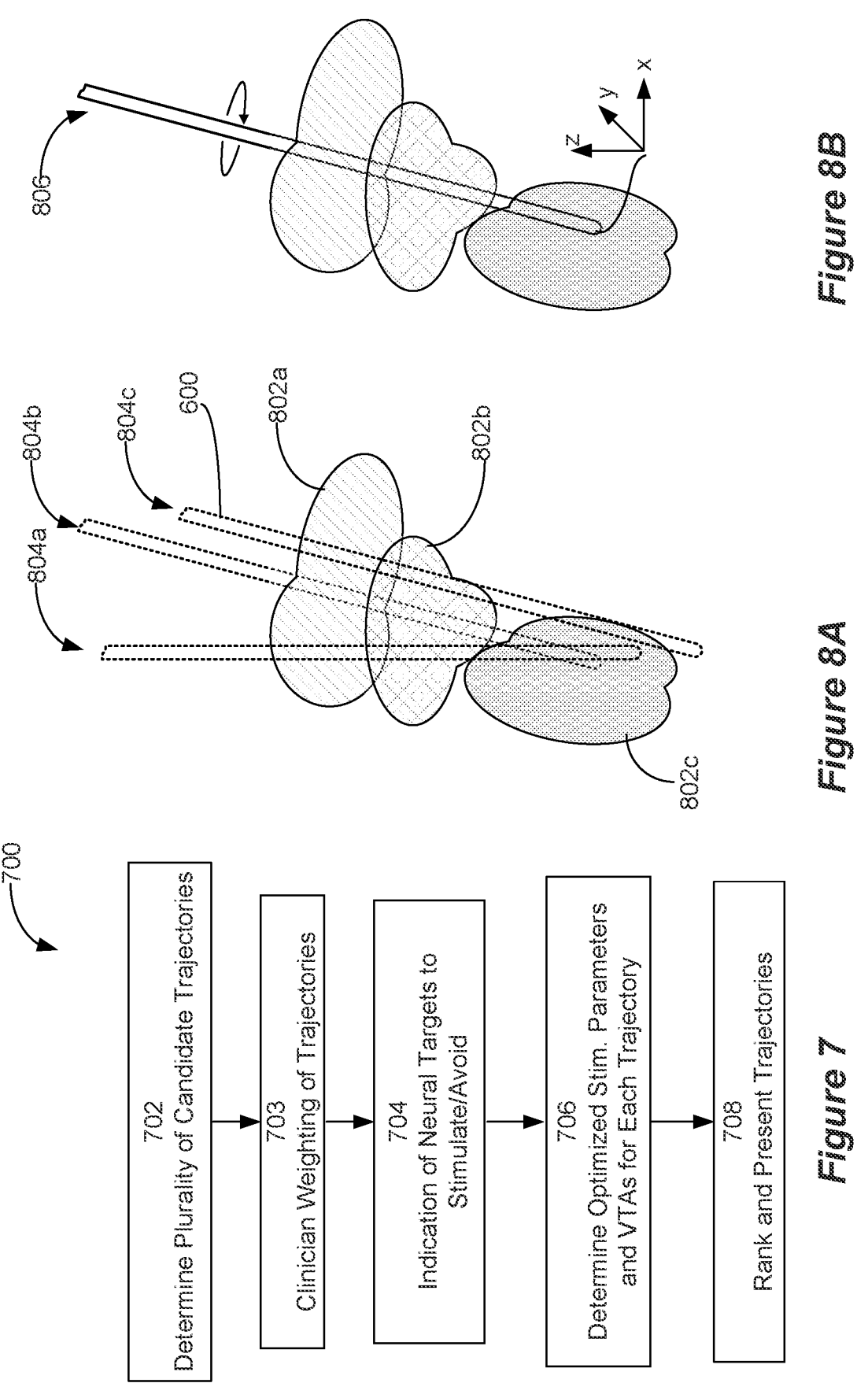
FIG. 7 shows an embodiment of a workflow for selecting a trajectory for a stimulation lead.
FIGS. 8A and 8B show trajectories for stimulation leads in contoured anatomical structures.

This disclosure relates to methods and systems that help a surgeon/physician evaluate potential DBS lead trajectories during the planning phase of an implantation procedure and to select a trajectory that best fits their needs. FIG. 7 shows an overview of one embodiment of a workflow 700 as described herein. Each of the components of the workflow will be discussed in more detail below. The workflow 700 may be executed with the aid of one or more computer programs running on a machine, as described in more detail below. The machine(s) may be configured to provide GUIs to aid in the selection and execution of steps of the workflow. The machines may be one or more, with processing and visualization potentially split, including portions on handheld phones, tablets, laptops, desktops, and servers, especially cloud servers, with access through dedicated applications (apps, software) or via web browser.

At step 702 the clinician may determine a plurality of candidate trajectories. According to some embodiments, the clinician may use computer-implemented planning algorithms to plan the plurality of candidate trajectories. The planning algorithms may be configured to use preoperative imaging to derive patient-specific atlas data for the patient. The preoperative imaging may comprise computed x-ray tomography (CT), a magnetic resonance tomography (MR), magnetic resonance imaging (MRI), positron emission tomography (PET), ultrasound tomography (sonography), and the like. The planning algorithms may be configured to contour particular anatomical structures such as the Subthalamic Nucleus (STN), Globus Pallidus Internal (GPI) and Ventral Intermediate (VIM) Nucleus. Examples of planning algorithms are described, for example, in U.S. Pat. Nos. 10,249,041 and 11,020,004, the contents of which are incorporated herein by reference. An example of a commercial product comprising algorithms for planning electrode lead trajectories is BRAINLAB ELEMENTS (Munich Germany), which is available with the Boston Scientific (Marlborough MA) VERCISE Deep Brain Stimulation family of systems.

Additionally, or alternatively, the system may determine a plurality of candidate trajectories. It may augment or automate the process of determining trajectories by using priors, e.g., a set of trajectories previously used by the surgeon, or a set curated for this purpose. Alternatively, the system my use an optimization scheme to use one or more starting trajectories to create, evaluate, and select a subset from a family of trajectories. Trajectories which meet certain criteria, such as passing within a distance of a target structure and avoiding an avoidance structure, may be chosen or used to create additional options.

FIG. 8 illustrates contour representations of three anatomical structures (802a, 802b, and 802c) as might be displayed on a graphical user interface (GUI) of a system configured for trajectory planning, as described above. In FIG. 8A the user has selected three candidate trajectories (804a, 804b, and 804c) for the electrode lead 600. FIG. 8B shows an embodiment wherein the user may select a plurality of trajectories by selecting a basis trajectory 806 and then specifying a variance in the tip position and in the longitudinal and rotational vectors (see FIG. 6). For example, the user may specify that the tip position, rotational vector, and longitudinal vector may each vary by ±10%. The system may be configured to select a given number of trajectories within the limits of the specified degree of variance.

Referring again to FIG. 7, once a plurality of trajectories have been posited, the clinician may rank or weight each of the trajectories (step 703). The weighting may be based on the clinician's experience and clinical judgement, for example. Some embodiments of the workflow may not include a step for the clinician ranking/weighting the trajectories. The system may also flag, tag, or highlight certain trajectories with useful information, or may sort the trajectories for clinician weighting, or may rank or weight the trajectories and allow clinician confirmation. The existence of prior surgeries, prior implanted materials, and especially prior implanted DBS leads may affect the operation of the software and the weighting of trajectories.

Figures 9, 10:
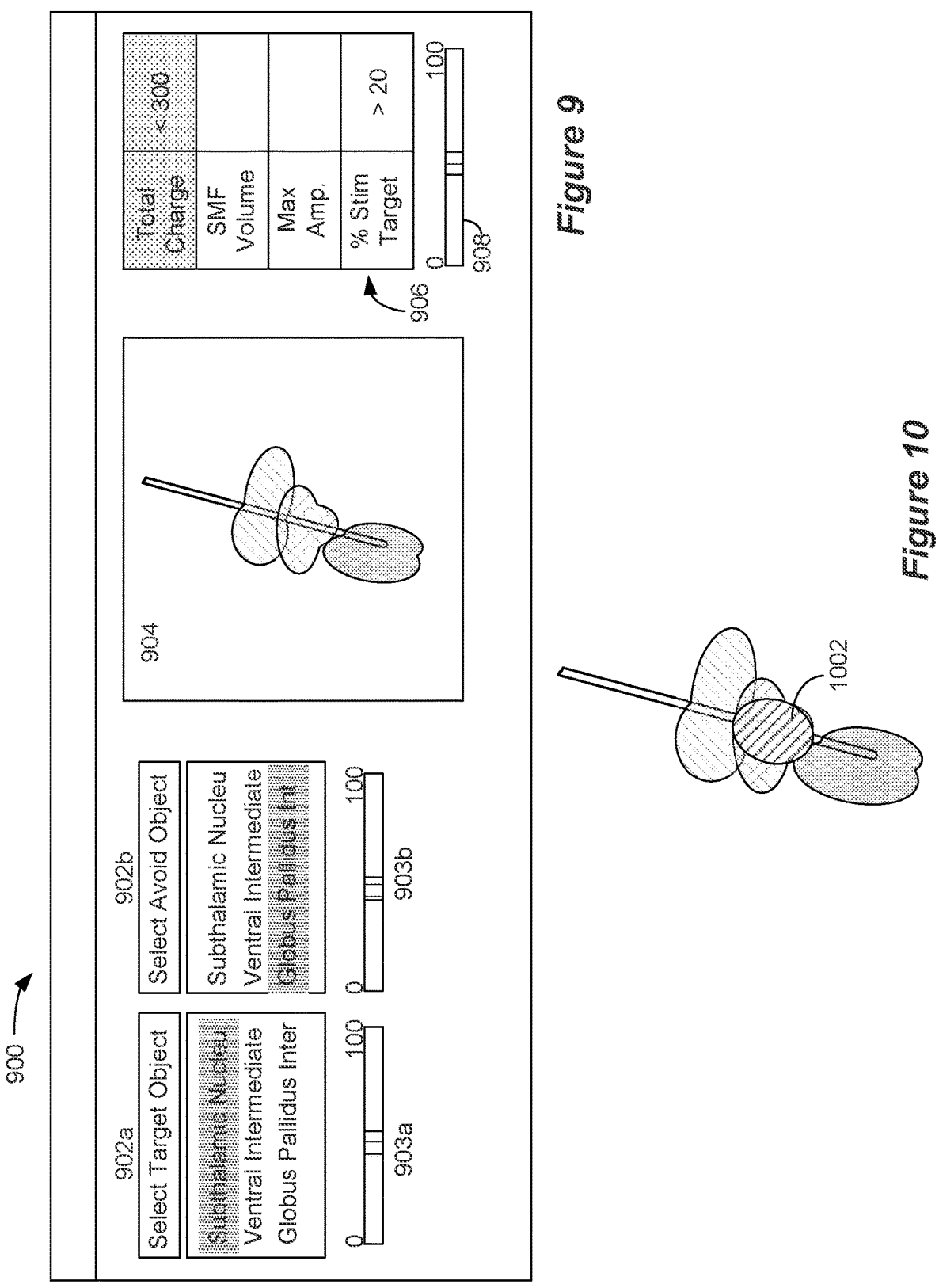
FIG. 9 shows a graphical user interface (GUI) for evaluating lead trajectories.
FIG. 10 shows a calculated volume of tissue activation (VTA).

At step 704 the clinician may specify which neural structures(s) are to be activated during the therapy and, possibly, which neural structures should not be activated. For example, referring to FIGS. 8A and/or 8B, the clinician may wish to provide stimulation that activates the anatomical structure 802b but that avoids activating the structures 802a and 802c (termed herein "avoidance structures"). FIG. 9 illustrates an embodiment of a GUI 900 having drop-down elements 902a and 902b that the clinician may use to select anatomical structures to activate and to avoid, respectively. These structures may be created from a patient imaging through a process such as automated segmentation, they may be created by refined segmented anatomy, or could be manually created by the clinician, or could be target volumes imported from some other workflow. In some cases, targets have a basis in anatomy, in others in physiology. The GUI may also include sliders 903a and 903b (or other GUI elements) for weighting the importance of the selected targets/non-targets structures. The GUI may also include be configured to display 904 a representation of the relevant anatomical structures (e.g., 802a, 802b, and 802c; FIG. 9). In the illustration, the display 904 also shows one of the candidate trajectories of a stimulation lead. The GUI 900 may also be configured to display GUI elements 906 whereby the user can select bounding parameters, or other desired parameters related to the stimulation, as will be discussed in more detail below.

Once the candidate trajectories (and their weights, if applicable) and the structures that should be stimulated and/or avoided have been indicated, at step 706 the algorithm may determine optimized stimulation parameters for each of the candidate trajectories. Also at step 706, the volume of tissue activated (VTA) is determined for one or more optimized stimulation parameters for each of the candidate trajectories. According to some embodiments, inverse programming algorithms may be used to automate the selection of optimized stimulation parameters. Given the indication of which target structures to stimulate and which ones to avoid (i.e., avoidance structures), the inverse programming algorithm may use stimulation field models (SFMs) to optimize the stimulation parameters so as to provide a VTA that best overlaps the desired structures and avoids the undesired ones. For the purposes of this disclosure, the terms SFM and VTA are considered as being equivalent. Specifically, the algorithms determine how current should be fractionalized among the electrodes to provide the optimum VTAs to preferentially stimulate the target. Additional stimulation parameters, such as (but not limited to) amplitude, pulse-width, pulse rate, pulse polarity, pulse type, or pattern may be considered. In some embodiments, multiple sets of stimulation parameters are searched and explored, and a subset are used for choosing trajectories, and information regarding the chosen settings are optionally presented to the clinician user, available for export to reports and other human and machine-readable formats, and available for systems to use in programming stimulation devices, including for intra-operative test use and chronic therapeutic use. When multiple target structures are present, additional weighting functions may be employed. The system may also create representations of expected responses which can be used to validate a preferred trajectory during implant, such as prediction of response with a lead partially or fully implanted, such responses including clinical responses to stimulation, including the induction of therapeutic and side effect responses to stimulation, as well as responses to recordable intracranial or other biopotentials, such as LFPs or Evoked Potentials recordable from the lead when partially or fully implanted according to a preferred trajectory. The system may consider secondary therapeutic and side-effect estimations, such as secondary therapeutic effects which become available in order to address stim-indued side effects resultant from primary therapeutic stimulation.

Algorithms for optimizing stimulation programs using SFMs/VTAs and patient-specific atlases and imaging are described in U.S. Pat. Nos. 11,344,732, 11,195,609, 9,411, 935, 9,072,905, and 8,958,615, the contents of which are incorporated herein by reference. An example of a commercial algorithm for optimizing stimulation programs using VTAs and patient-specific atlases and imaging is Boston Scientific's Illumina 3-D algorithm (Boston Scientific, Valencia, CA, USA). It should be noted that the Illumina 3-D algorithm and the algorithms described in the incorporated references are generally used intra- and post-operatively, that is, after leads are implanted in the patient's brain. Once the lead is implanted, post-operative imaging and those algorithms can be used to optimize stimulation parameters based on the implanted lead's position. By contrast, the instant application uses the inverse programming algorithms to determine VTAs for prospective candidate trajectories.

Figures 1A, 1B, 1C:
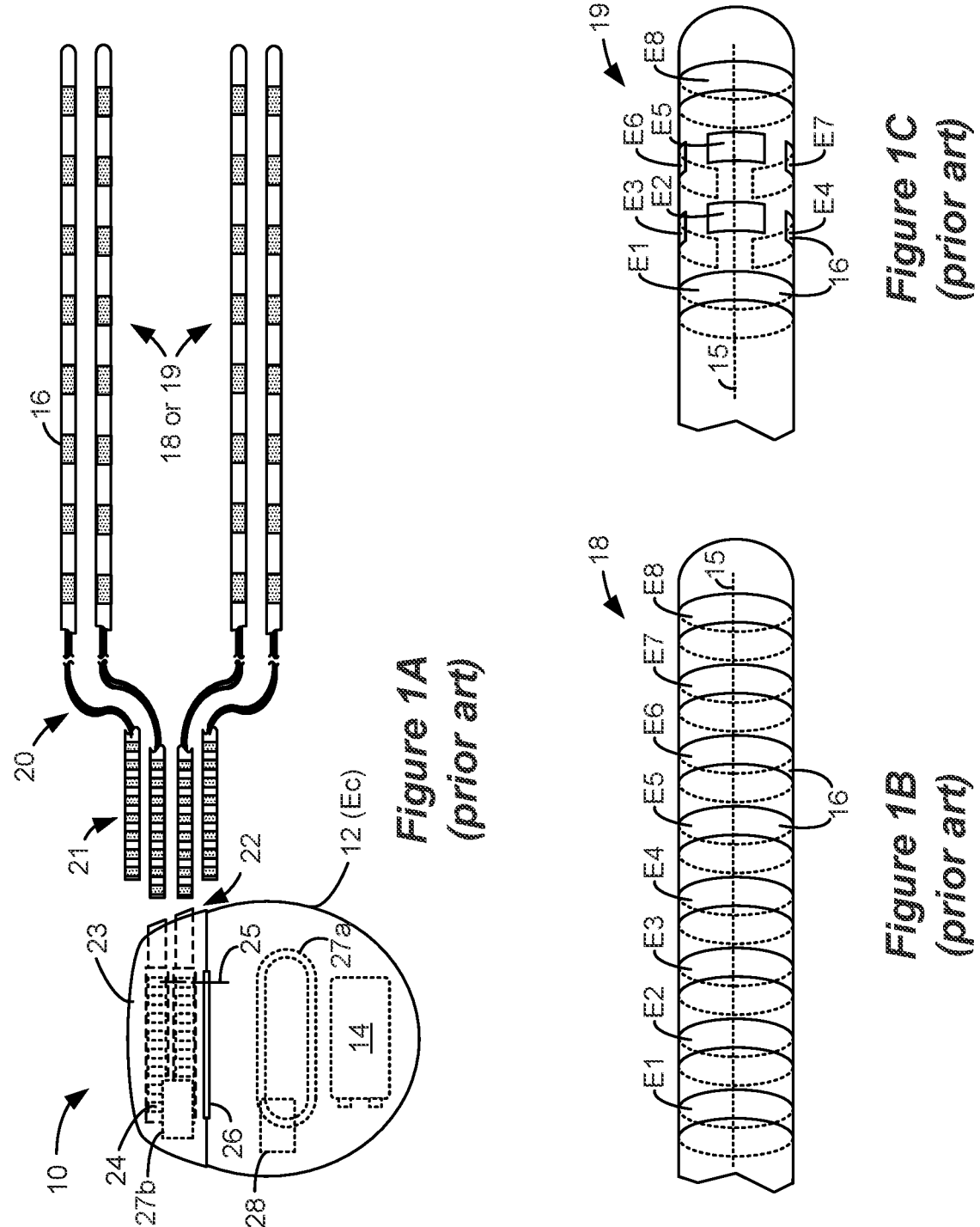
FIG. 1A shows an Implantable Pulse Generator (IPG), in accordance with the prior art.
FIG. 1B shows a percutaneous lead having ring electrodes.
FIG. 1C shows a percutaneous lead having split ring electrodes, in accordance with the prior art.
Figures 2A, 2B, 3:
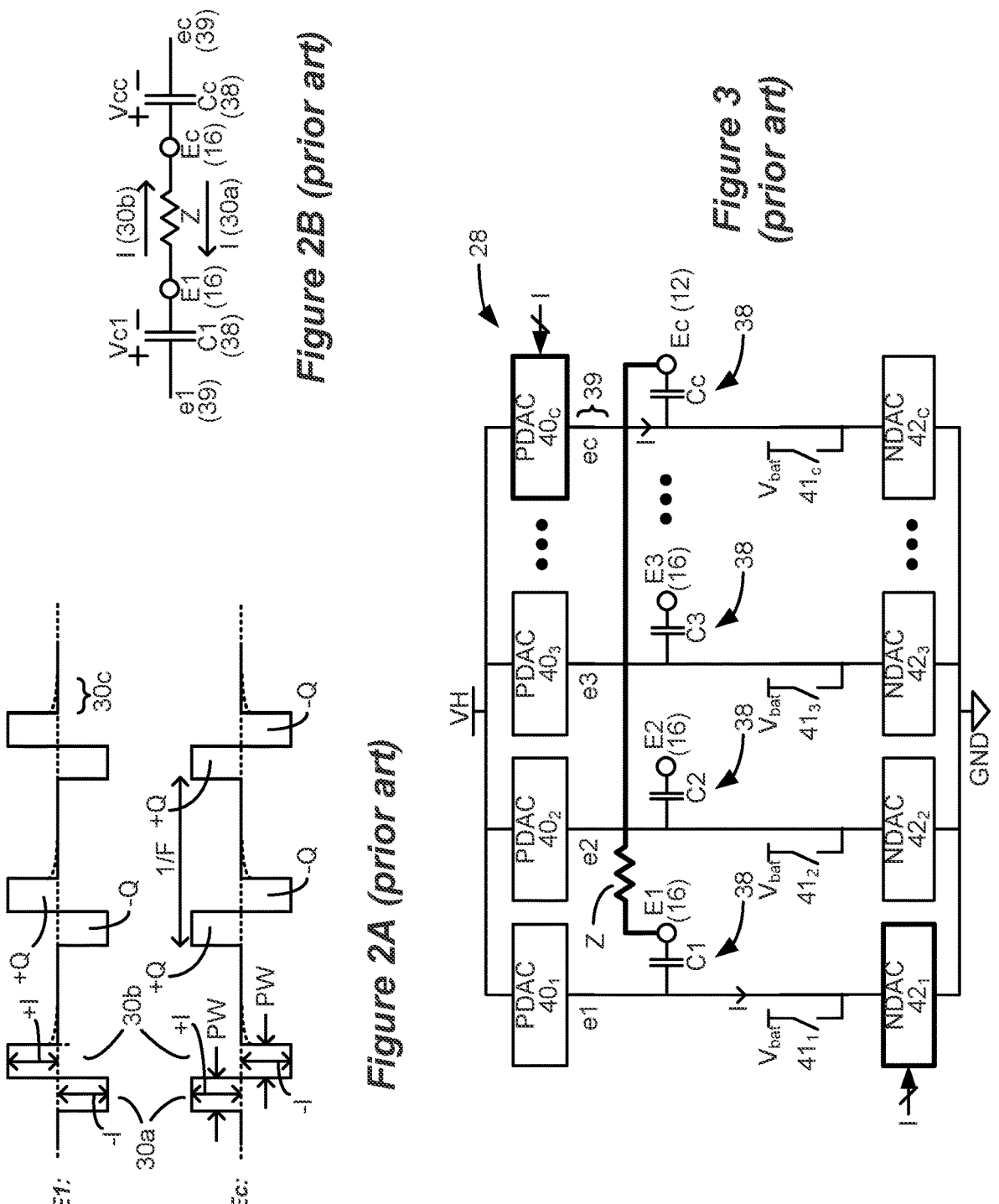
FIGS. 2A and 2B show an example of stimulation pulses (waveforms) producible by the IPG, in accordance with the prior art.
FIG. 3 shows an example of stimulation circuitry useable in the IPG, in accordance with the prior art.
Figure 4:
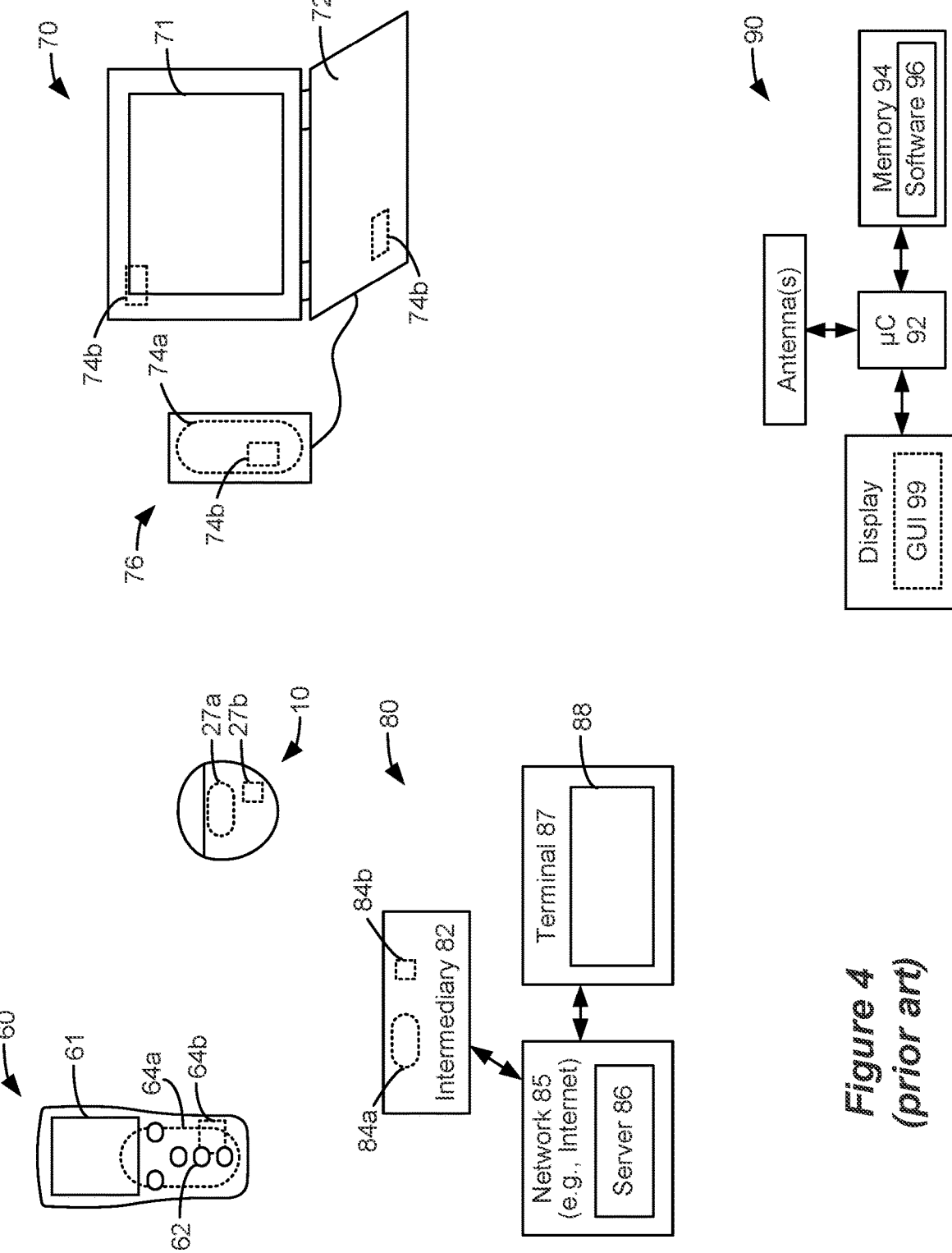
FIG. 4 shows various external systems capable of communicating with and programming stimulation in an IPG, in accordance with the prior art.
Figure 5A:
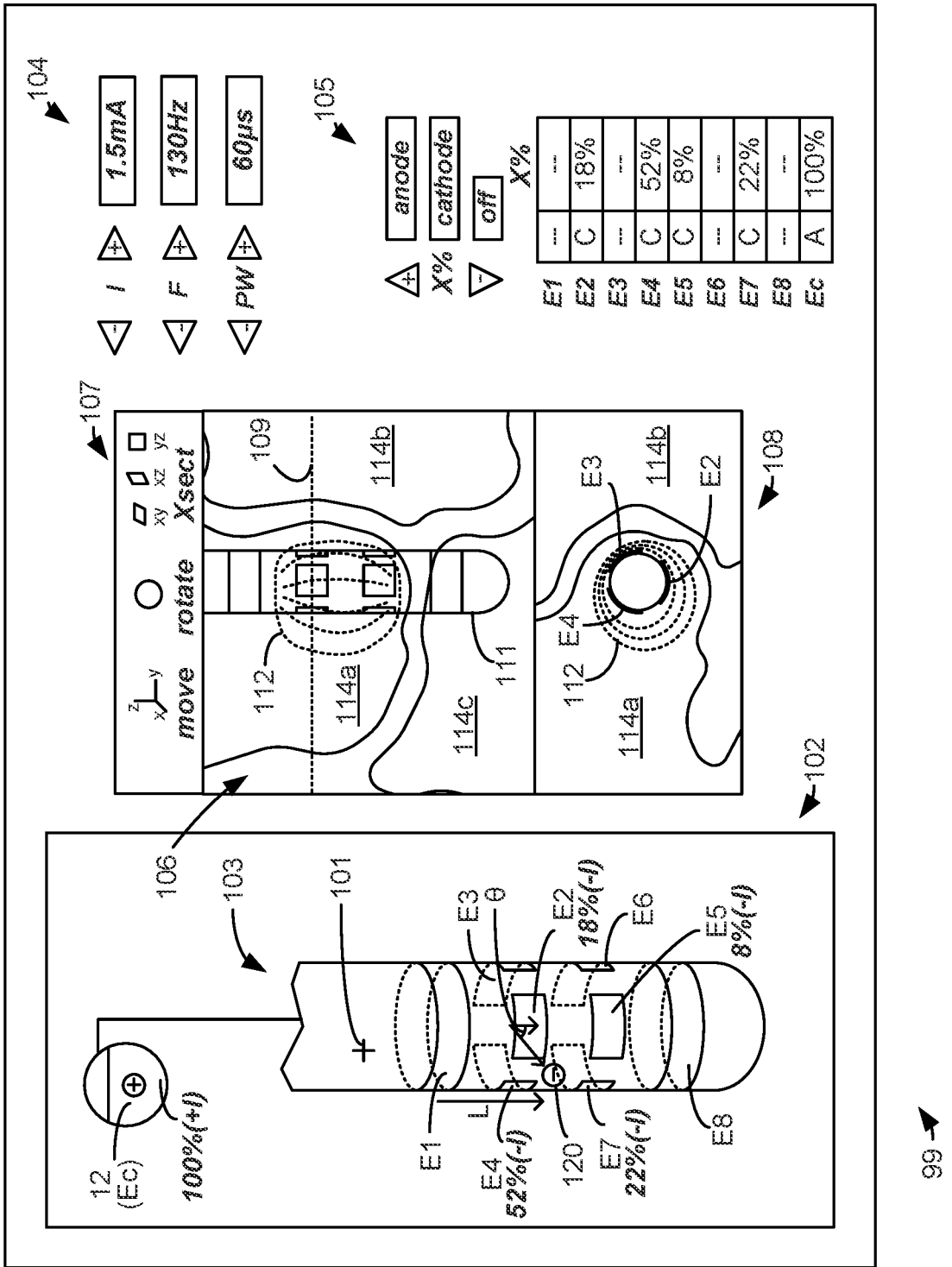
FIG. 5A shows a Graphical User Interface (GUI) operable on an external system such as a clinician programmer, which is capable of programming a stimulation program for the IPG.

As mentioned above, the inverse programming algorithm (s) may operate on each of the candidate trajectories to determine an optimized "fractionalization" of currents for the electrodes when the lead is in that candidate trajectory. The fractionalization may be expressed as a percentage of the total current provided to each active electrode (see, e.g., FIG. 5A). To generate the VTA associated with each fractionalization, electric fields resulting from the stimulation setting are constructed as finite element models (FEMs), for example, using programs such as COMSOL Multiphysics software (COMSOL Inc., Burlington, MA, USA). The lead body and the neural tissue may be modeled, as known in the art. A multi-resolute mesh may be created to encompass both the lead body and the surrounding tissue, with highest resolution at electrode-tissue interface and higher resolution in a region of interest (ROI) surrounding the electrode array versus the remaining volume. The scalar potentials at the mesh nodes are calculated and the model is solved once per electrode at unit current (1 mA).

The electric field results from the RoI can be interpolated onto a regular grid of model axons that surround the DBS lead. The response to each stimulus can be computed by temporally scaling the potentials along the axon compartments using a waveform modeled on stimulator recordings to estimate the threshold current ('Ith', in mA) at which each axon in the grid fires an action potential from quiescence. A machine learning algorithm (Bootstrap Aggregated Random Forest) which takes features of the axon voltage profile as input and estimates axon's response can be trained, for example, on over 100 million axon simulations. Basis files and the trained predictor can be integrated with the anatomical model of the patient. The output current amplitude thresholds for the axon models are iso-surfaced at the selected stimulation current amplitude. The resulting surface can be displayed as the VTA and overlayed with the representation of the patient's anatomy, if desired. FIG. 10 illustrates an example of an VTA 1002 corresponding to a particular set of stimulation parameters overlayed over the display of the anatomical structures, as described above.

Embodiments of the reverse programming algorithm may use a metric optimization algorithm, such as Bound Optimization by Quadratic Approximation (BOBQYA). The goal of the algorithm is to maximize stimulation of a target volume while staying within clinician-specified constraints. The algorithm incorporates the cost of increasing the size of the VTA, the cost of overlapping with avoidance volumes, including possible side effect regions, as well as stimulation safety limits.

The cost function, or metric, for the optimizer, for each fractionalization, is a weighted summation of the stimulated volumes for each structure (one target and one or more avoidance regions) and the VTA (background volume). The Target structure has a positive weight, and the avoidance structures and background have negative weights. The target and avoidance structures can be in the form of probabilistic maps such that with constant weights some portions of the structures could have higher or lower calculated overlap scores. In addition, in some implementations, the weights can be unequally distributed throughout the volume of each structure, such that overlapping with some portions results in higher or lower calculated overlap scores than others. For each fractionalization, the highest possible metric value is calculated, and the corresponding amplitude is determined. The clinician can specify one target region, zero or more avoidance region(s), the priority of not stimulating the avoidance regions (controlled by a slider to set 'avoidance ratio'), and prioritization of reduced VTA volume (controlled by a slider to set the 'background ratio'). The equation to calculate the optimized metric is therefore:

$$m = \Sigma(v_{target} - (v_{avoidance} * \text{avoidance ratio}) - (v_{SFM} * \text{background ratio}))$$

Where:

m=metric value, $v_{target}$=stimulated target volume in mm$^3$, $v_{avoidance}$=stimulated avoidance volume in mm$^3$, and $v_{SFM}$=total VTA volume in mm$^3$, In summary, the metric is the sum of the stimulated target volume (in mm$^3$) minus the total volume of stimulated avoidance region (in mm$^3$), weighted by the avoidance ratio, minus the total volume of background stimulation (in mm$^3$), weighted by the background ratio. Where the avoidance ratio is the ratio of the cost (reduction in metric value) of stimulating avoidance region to the benefit (increase in metric value) of stimulating target region, and the background ratio is the ratio of the cost of stimulating background volume to the benefit of stimulating target region. The stimulated background volume is the same as the volume of the VTA.

The optimization algorithm may be run once for each of two Virtual Electrode (see below) types (one equivalent to the ring electrodes on the lead, and one equivalent to the segmented electrodes on the lead, but with arbitrary placement and rotation). First, the optimizer is run using the ring virtual electrode, and a best solution is determined. If the lead is directional, the optimizer is run using the directional virtual electrode. As the optimization algorithm tests each virtual electrode's position, the position is converted to a fractionalization on the real electrodes of the lead. For each fractionalization, the best metric among the possible amplitudes is compared to the metric of the current best solution. If the new metric is better than the previous best metric, the new metric, virtual electrode type, position, and derived amplitude are stored as the new best solution. When the optimization algorithm has met the stop conditions the best solution is returned and displayed for the clinician.

According to some embodiments, a Virtual Electrode is a ring (e.g., 1.5 mm height and 360 degrees around the lead) or directional (e.g., 1.5 mm height and 90 degrees around the lead) electrode that, for the calculation of the electrode's voltage field, is modeled as the only electrode on a lead of infinite length with the same nominal lead diameter and material as a real lead. The Virtual Electrode's voltage field is rotated around the axis of the lead and translated along the axis of the lead to model the placement of the virtual electrode at some arbitrary location along and around the active length of the lead. Least-squares fitting is used to determine the fractionalization on the real electrodes that would produce the best fit between the voltage field generated by the real electrodes on the real lead and the voltage field of the virtual electrode placed at the selected location.

According to other embodiments, the algorithm may involve "brute-force" searching for optimum stimulation parameters for each of the candidate trajectories, rather than using a reverse programming algorithm. In other words, for each of the candidate trajectories, the clinician may try a series of fractionalizations to determine which ones best overlap with the desired anatomical target.

Referring again to the workflow 700 (FIG. 7), the above discussion explains how optimized parameters stimulation parameters and the overlap of the VTAs with the target anatomical structures can be determined for each of the candidate trajectories can be determined. Step 708 involves ranking and presenting the candidate trajectories based on their VTAs (under optimized stimulation parameters) and their a priori clinician weighting (if available). According to some embodiments, the algorithm includes a search engine configured to rank and weight the candidate trajectories based on those criteria.

FIG. 11 illustrates an example of the ranking/weighting. Assume that the clinician has posited three candidate trajectories—804*a*, 804*b*, and 804*c*, as indicated in the list 1102. Also assume that the clinician has weighted each of the trajectories as reflected in FIG. 11. That weighting indicates that the clinician believes that the trajectory 804*a* will be the best trajectory. The clinician's belief may be based on experience, historical data, published data, or the like. For example, a given trajectory may be known to best avoid vasculature, ventricles, etc. As mentioned above, some embodiments may not include the step of receiving a clinician's weighting. In some embodiments, the clinician may weight or first weight considerations that the algorithm will use when finding, sorting, ranking, scoring trajectories. For example, the clinician might weight 'avoidance of vascular effect' high, and 'avoidance of induction of cognitive decline' low in a given patient.

As explained above, the algorithm determines the optimum stimulation parameters (step 706, FIG. 7) for each of the candidate trajectories. The optimum stimulation parameters are informed by the clinician's specification of which anatomical features should be stimulated and which ones should be avoided. The algorithm also determines the VTAs that are achievable for each of the candidate trajectories, based on the optimized stimulation parameters. Once the VTAs are determined for each trajectory, the algorithm may apply a search engine and/or sorting routine to rank the candidate trajectories based on which ones provide the best VTAs while considering the clinician's a priori rankings (if available). In the illustrated example, as reflected in the list 1104, the search engine determined that the trajectory 804*b* should be ranked highest. Note that that determination is different from the one the clinician chose as the first option.

According to some embodiments, the ranking algorithms may consider other criteria, constraints, bounding parameters, and the like (which are collectively referred to herein as "bounding parameters"). Examples of bounding parameters may relate to power usage, stimulation amplitude, total charge, pulse width, frequency, or effects on the patient, such as risk of induced side effects, etc. For example, in some situations the clinician may wish to use the minimum energy to get the maximum benefit. In that scenario, the clinician may select a bounding parameter based on energy usage. For example, the algorithm can be configured weight energy usage relatively heavily. In other situations, the clinician may not care about energy usage and may simply want to use the trajectory that provides the best VTA overlap, regardless of the energy usage. In another scenario, the clinician may want to set a boundary parameter that the stimulation does not exceed a pre-defined amplitude. Other examples of boundary parameters will be apparent to a person of skill in the art.

As mentioned above, the GUI 900 (FIG. 9) may include GUI elements, such as element 906 for selecting various bounding parameters. According to some embodiments, the GUI elements may include a slider 908 (or some other element) to rank the importance (i.e., the weighting) of the selected boundary parameters. For example, in the embodiment illustrated in FIG. 9, the user has selected "Total Charge" as a bounding parameter and does not wish the charge to exceed 300 Coulombs. The user may use the slider 908 to set how strongly the algorithm weights the Total Charge bounding parameter. When bounding parameters are selected, the parameter optimization algorithm(s) may be constrained to only considering stimulation parameters (and corresponding VTAs) within the bounded domain. Alternatively (or additional), the search engine may weight candidate trajectories based on the selected bounding parameters (i.e., giving favorable weightings to trajectories that provide usable VTAs while complying with the bounding parameters).

FIG. 12 illustrates generally a block diagram of an example machine 1200 upon which any one or more of the techniques (e.g., algorithms, methodologies, etc.) discussed herein may perform. In alternative embodiments, the machine 1200 may operate as a standalone device or may be connected (e.g., networked) to other machines. In a networked deployment, the machine 1200 may operate in the capacity of a server machine, a client machine, or both in server-client network environments. In an example, the machine 1200 may act as a peer machine in peer-to-peer (P2P) (or other distributed) network environment. The machine 1700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specific operations when operating. In an example, hardware of the circuit set may be immutably designed to carry out a specific operation (e.g., hardwired), in an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1200 may include a hardware processor 1202 (e.g., a central processing unit (CPU), a graphics processing unit (GPU), a hardware processor core, or any combination thereof), a main memory 1204 and a static memory 1206, some or all of which may communicate with each other via an interlink (e.g., bus) 1208. The machine 1200 may further include a display unit 1210 (e.g., a raster display, vector display, holographic display, etc.), an alphanumeric input device 1212 (e.g., a keyboard), and a user interface (UI) navigation device 1214 (e.g., a mouse). In an example, the display unit 1210, input device 1212 and UI navigation device 1214 may be a touch screen display. The machine 1200 may additionally include a storage device (e.g., drive unit) 1216, a signal generation device 1218 (e.g., a speaker), a network interface device 1220, and one or more sensors 1221, such as a global positioning system (GPS) sensor, compass, accelerometer, or other sensors. The machine 1200 may include an output controller 1228, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1216 may include a machine readable medium 1222 on which is stored one or more sets of data structures or instructions 1224 (e.g., software) embodying or utilized by any one or more of the techniques or functions described herein. The instructions 1224 may also reside, completely or at least partially, within the main memory 1204, within static memory 1206, or within the hardware processor 1202 during execution thereof by the machine 1700. In an example, one or any combination of the hardware processor 1202, the main memory 1204, the static memory 1206, or the storage device 1216 may constitute machine readable media.

While the machine readable medium 1222 is illustrated as a single medium, the term "machine readable medium" may include a single medium or multiple media (e.g., a centralized or distributed database, and/or associated caches and servers) configured to store the one or more instructions 1224. The term "machine readable medium" may include any medium that is capable of storing, encoding, or carrying instructions for execution by the machine 1200 and that cause the machine 1200 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1224 may further be transmitted or received over a communications network 1726 using a transmission medium via the network interface device 1220 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1220 may include one or more physical jacks (e.g., Ethernet, coaxial, or phone jacks) or one or more antennas to connect to the communications network 1226. In an example, the network interface device 1220 may include a plurality of antennas to wirelessly communicate using at least one of single-input multiple-output (SINK)), multiple-input multiple-output (MIMO), or multiple-input single-output (MISO) techniques. The term "transmission medium" shall be taken to include any intangible medium that is capable of storing, encoding or carrying instructions for execution by the machine 1200, and includes digital or analog communications signals or other intangible medium to facilitate communication of such software.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for planning a position for a stimulation lead for neurostimulation of one or more target structures of a patient's brain, wherein the stimulation lead comprises a tip, a longitudinal axis, and a plurality of electrode contacts, wherein the method is executable using a machine comprising a user interface (UI) and a processor, the method comprising:

receiving, via the UI, an indication of the one or more target structures, receiving, via the UI, indications of a plurality of candidate positions for the stimulation lead;

using the processor to:

execute a reverse programming algorithm to determine a set of optimized stimulation parameters for each of the candidate positions based on the target structures;

predict a volume of tissue activated (VTA) for each of the candidate positions' set of optimized stimulation parameters;

determine an overlap of each of the predicted VTA with the target structure, and rank the plurality of candidate positions based at least partially on the overlaps, and present an indication of the ranking of each of the plurality of candidate positions on the UI.

2. The method of claim 1, wherein each candidate position is defined by a tip location, a rotation angle, and a longitudinal axis angle.

3. The method of claim 2, wherein the indication of a plurality of candidate positions comprises an indication of a basis position and of values for one or more of the tip location, rotation angle, and/or longitudinal axis angle.

4. The method of claim 1, wherein the reverse programming algorithm comprises optimizing current fractionalization among the electrode contacts based on stimulation field models (SFMs) modeled for each current fractionalization.

5. The method of claim 4, wherein the reverse programming algorithm comprises a cost function that includes (i) overlap of the SFMs with the target structure for each current fractionalization, and (ii) a cost associated with increasing a size of the SFM.

6. The method of claim 5, wherein the cost function is further a function of (iii) overlap of the SFMs with an avoidance structure for each current fractionalization.

7. The method of claim 1, wherein ranking the plurality of candidate positions is further based on one or more bounding parameters or additional scoring functions.

8. The method of claim 7, wherein the bounding parameters comprise maximum power usage.

9. The method of claim 7, wherein the bounding parameters specify one or more of stimulation amplitude values, total charge values, pulse width, or frequency.

10. An apparatus for planning a position for a stimulation lead for neurostimulation of one or more target structures of a patient's brain, wherein the stimulation lead comprises a tip, a longitudinal axis, and a plurality of electrode contacts, the apparatus comprising:
   a user interface (UI), and
   a processor configured to:
      receive, via the UI, an indication of the one or more target structures,
      receive, via the UI, indications of a plurality of candidate positions for the stimulation lead;
      execute a reverse programming algorithm to determine a set of optimized stimulation parameters for each of the candidate positions based on the target structures;
      predict a volume of tissue activated (VTA) for each of the candidate positions' set of optimized stimulation parameters;

determine an overlap of each of the predicted VTA with the target structure,
rank the plurality of candidate positions based at least partially on the overlaps, and
present an indication of the ranking of each of the plurality of candidate positions on the UI.

11. The apparatus of claim 10, wherein each candidate position is defined by a tip location, a rotation angle, and a longitudinal axis angle.

12. The apparatus of claim 11, wherein the indication of a plurality of candidate positions comprises an indication of a basis position and of values for one or more of the tip location, rotation angle, and/or longitudinal axis angle.

13. The apparatus of claim 10, wherein the reverse programming algorithm comprises optimizing current fractionalization among the electrode contacts based on stimulation field models (SFMs) modeled for each current fractionalization.

14. The apparatus of claim 13, wherein the reverse programming algorithm comprises a cost function that includes (i) overlap of the SFMs with the target structure for each current fractionalization, and (ii) a cost associated with increasing a size of the SFM.

15. The apparatus of claim 14, wherein the cost function is further a function of (iii) overlap of the SFMs with an avoidance structure for each current fractionalization.

16. The apparatus of claim 10, wherein ranking the plurality of candidate positions is further based on one or more bounding parameters.

17. The apparatus of claim 16, wherein the bounding parameters comprise maximum power usage.

18. The apparatus of claim 16, wherein the bounding parameters specify one or more of stimulation amplitude values, total charge values, pulse width, or frequency.

* * * * *